United States Patent
Everhart et al.

(12)

(10) Patent No.: US 6,573,040 B2
(45) Date of Patent: *Jun. 3, 2003

(54) PATTERNED BINDING OF FUNCTIONALIZED MICROSPHERES FOR OPTICAL DIFFRACTION-BASED BIOSENSORS

(75) Inventors: Dennis S. Everhart, Alpharetta, GA (US); Rosann M. Kaylor, Cumming, GA (US); Kevin McGrath, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 41 days.

This patent is subject to a terminal disclaimer.

(21) Appl. No.: 09/733,204

(22) Filed: Dec. 8, 2000

(65) Prior Publication Data
US 2001/0004526 A1 Jun. 21, 2001

Related U.S. Application Data (62) Division of application No. 09/210,016, filed on Dec. 11, 1998, now Pat. No. 6,221,579.

(51) Int. Cl.$^7$ ............................................. G01N 33/567
(52) U.S. Cl. ............................ 435/5; 435/7.21; 435/291
(58) Field of Search ............................. 435/5, 7.21, 291

(56) References Cited

U.S. PATENT DOCUMENTS 5,512,131 A * 4/1996 Kumar et al. ............ 156/655.1
6,221,579 B1 * 4/2001 Everhart et al. ................ 435/5

* cited by examiner

Primary Examiner—Michael Borin
(74) Attorney, Agent, or Firm—Kilpatrick Stockton LLP

(57) ABSTRACT

The present invention provides an inexpensive and sensitive system and method for detecting analytes present in a medium. The system comprises a diffraction enhancing element, such as functionalized microspheres, which are modified such that they are capable of binding with a target analyte. Additionally, the system comprises a polymer film, which may include a metal coating, upon which is printed a specific, predetermined pattern of a analyte-specific receptors. Upon attachment of a target analyte to select areas of the polymer film, either directly or with the diffraction enhancing element, diffraction of transmitted and/or reflected light occurs via the physical dimensions and defined, precise placement of the analyte. A diffraction image is produced which can be easily seen with the eye or, optionally, with a sensing device.

37 Claims, 3 Drawing Sheets

Fig_1

Fig_2

PATTERNED BINDING OF FUNCTIONALIZED MICROSPHERES FOR OPTICAL DIFFRACTION-BASED BIOSENSORS

This is a divisional of U.S. patent application Ser. No. 09/210,016, filed Dec. 11, 1998, now U.S. Pat. No. 6,221,579.

TECHNICAL FIELD

The present invention is generally in the field of detecting analytes in a medium and, more particularly, the present invention relates to the use of functionalized microspheres for enhancing optical diffraction with single use, disposable sensors to indicate the presence of the analyte in a medium.

BACKGROUND OF THE INVENTION

There are many systems and devices available for detecting a wide variety of analytes in various media. Most of these systems and devices are relatively expensive and require a trained technician to perform the test. There are many cases where it would be advantageous to be able to rapidly and inexpensively determine if an analyte were present. What is needed is a biosensor system that is easy and inexpensive to manufacture and is capable of reliable and sensitive detection of analytes, including smaller analytes.

Sandstrom et al., 24 *Applied Optics* 472, 1985, describe use of an optical substrate of silicon with a layer of silicon monoxide and a layer of silicon formed as dielectric films. They indicate that a change in film thickness changes the properties of the optical substrate to produce different colors related to the thickness of the film. The thickness of the film is related to the color observed and a film provided on top of an optical substrate may produce a visible color change. The authors indicate that a mathematical model can be used to quantitate the color change, and that "[c]alculations performed using the computer model show that very little can be gained in optical performance from using a multi-layer structure . . . but a biolayer on the surface changes the reflection of such structures very little since the optical properties are determined mainly by the interfaces inside the multilayer structure. The most sensitive system for detection of biolayers is a single layer coating, while in most other applications performance can be by additional dielectric layers."

Sandstrom et al., go on to indicate that slides formed from metal oxides on metal have certain drawbacks, and that the presence of metal ions can also be harmful in many biochemical applications. They indicate that the ideal top dielectric film is a 2–3 nm thickness of silicon dioxide which is formed spontaneously when silicon monoxide layer is deposited in ambient atmosphere, and that a 70–95 nm layer silicon dioxide on a 40–60 nm layer of silicon monoxide can be used on a glass or plastic substrate. They also describe formation of a wedge of silicon monoxide by selective etching of the silicon monoxide, treatment of the silicon dioxide surface with dichlorodimethylsilane, and application of a biolayer of antigen and antibody. From this wedge construction they were able to determine film thickness with an ellipsometer, and note that the "maximum contrast was found in the region about 65 nm where the interference color changed from purple to blue." They indicate that the sensitivity of such a system is high enough for the detection of protein antigen by immobilized antibodies. They conclude "the designs given are sensitive enough for a wide range of applications". The materials, i.e., glass, silicon, and silicon oxides, are chemically inert and do not affect the biochemical reaction studied. Using the computations above it is possible to design slides that are optimized for different applications. The slides can be manufactured and their quality ensured by industrial methods, and two designs are now commercially available.

U.S. Pat. No. 5,512,131 issued to Kumar et al. describes a device that includes a polymer substrate having a metal coating. An analyte-specific receptor layer is stamped on the coated substrate. The device is used in a process for stamping or as a switch. A diffraction pattern is generated when an analyte binds to the device. A visualization device, such as a spectrometer, is then used to determine the presence of the diffraction pattern.

However, the device described by Kumar et al. has several disadvantages. One disadvantage is that an extra visualization device is needed to view any diffraction pattern. By requiring a visualization device, the Kumar et al. device does not allow a large number of samples to be tested since it is not possible to determine the presence of an analyte by using the unaided eye. Additionally, this device is not able to detect smaller analytes as these analytes do not produce a noticeable diffraction pattern.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color (by having a combination of wavelengths of light which differ from that combination present in the first color, or having a different spectral distribution, or by having an intensity of one or more of those wavelengths different from those present in the first color). The second color is exhibited in response to the same light when the analyte is present on the surface. The change from one color to another can be measured either by use of an instrument, or by eye. Such sensitive detection is an advance over the devices described by Sandstrom and Nygren, supra, and allow use of the devices in commercially viable and competitive manner.

However, the method and device described in the Bogart, et al. patent has several disadvantages. One disadvantage is the high cost of the device. Another problem with the device is the difficulty in controlling the various layers that are placed on the wafer so that one obtains a reliable reading.

Additionally, biosensors having a self-assembling monolayer have been used to detect analytes and are set forth in U.S. patent application Ser. Nos. 08/768,449 and 08/991,844, both of which are incorporated herein by reference in their entirety. However, these biosensors currently do not have the requisite sensitivity required to detect smaller analytes since these smaller analytes do not produce a sufficient diffraction pattern to be visible.

Some commercial lateral flow technologies have been used which employ latex bead technology. These technologies are currently employed in most of the commercially-available home diagnostic kits (e.g. pregnancy and ovulation kits). These kits use colored beads which accumulate in a defined "capture zone" until the amount of beads becomes visible to the unaided eye. However, these systems lack the requisite sensitivity to test for many analytes, since a much larger number of latex beads must bind in the capture zone to be visible to the naked eye than that required to cause diffraction in the same size zone. Generally, the number of beads needed is about 2 to 3 orders of magnitude higher than the sensors of the present invention.

What is needed is a biosensor system that is easy and inexpensive to manufacture and is capable of reliable and sensitive detection of analytes, including smaller analytes.

SUMMARY OF THE INVENTION

The present invention provides an inexpensive and sensitive system and method for detecting analytes present in a medium. The system comprises a biosensing device having a polymer film upon which is printed a specific, predetermined pattern of analyte-specific receptors. The polymer film may be coated with a metal layer. Additionally, the system utilizes "diffraction enhancing elements" which are capable of binding to the target analyte and to the biosensor and are capable of producing a substantial change in the height and/or refractive index, thereby increasing the diffraction efficiency of the biosensor and permitting the detection of smaller analytes. In use, a target analyte attaches either to the diffraction enhancing element, which then attaches to the biosensor, or directly to select areas of the polymer film upon which the receptor is printed. Then diffraction of transmitted and/or reflected light occurs via the physical dimensions and defined, precise placement of the analyte. A diffraction image is produced which can be easily seen with the eye or, optionally, with a sensing device.

The system of the present invention is much more sensitive than current inexpensive systems. The system of the present invention is able to detect low to high molecular weight analytes, microorganisms, and DNA or RNA species in fluid samples. More specifically, the system is able to detect hormones, steroids, antibodies, drug metabolites, and even nucleic acids, among others. This is a significant expansion of the optical diffraction-based sensing technology set forth in U.S. patent application Ser. Nos. 08/768,449 and 08/991,844.

The present invention utilizes diffraction enhancing elements, such as latex microspheres, which aid in the detection of smaller analytes. Normally, after an analyte binds to an analyte-specific receptor on a biosensor, the analyte will diffract or reflect transmitted light to produce a diffraction pattern. If the analyte is larger, the diffraction pattern is able to be seen with the unaided eye. However, some analytes are too small such that the diffraction pattern produced is not able to be seen. By using diffraction enhancing elements, the biosensor having the analyte-specific receptor material may be used to detect these smaller analytes. The diffraction enhancing elements used are capable of binding to the analyte, and then the element with bound analyte binds to the biosensor. Then, as the light is transmitted through or reflected from the biosensor, the element enhances the diffraction pattern generated by the analyte such that the resulting diffraction pattern may be seen by the unaided eye.

The present invention also utilizes methods of contact printing of patterned, analyte-specific receptors. The analyte-specific receptors have receptive materials bound thereto. The receptive materials are specific for a particular analyte or class of analyte, depending upon the receptor used. Methods of contact printing which would be useful in generating the sensing devices used in the present system are disclosed fully in U.S. patent application Ser. Nos. 08/707,456 and 08/769,594, both of which are incorporated herein by reference in their entirety. However, since these methods relate to self-assembling monolayers, the methods need to be altered slightly, as discussed below, to print the analyte-specific receptor material as this material is not self-assembling.

Patterned analyte-specific receptor layers allow for the controlled placement of analytes and/or diffraction enhancing elements thereon via the patterns of analyte-specific receptors. The biosensing devices of the present invention produced thereby are used by first exposing the biosensing device to a medium that contains the analyte of choice mixed with the diffraction enhancing element. Then, after an appropriate incubation period, a light, such as a laser or other point light source, is transmitted through or reflected from the film. If the analyte is present in the medium and is bound, either directly or in conjunction with the diffraction enhancing element, to the receptors on the patterned analyte-specific receptor layer, the light is diffracted in such a way as to produce a visible image. In other words, the analyte-specific receptor layers with the analyte and/or diffraction enhancing element bound thereto can produce optical diffraction patterns which differ depending on the reaction of the receptors on the analyte-specific receptor layer with the analyte of interest. The light can be in the visible spectrum, and be either reflected from the film, or transmitted through it, and the analyte can be any compound or particle reacting with the analyte-specific receptor layer. The light can be a white light or monochromatic electromagnetic radiation in the visible region. While visible light is the desired light source, the present invention may also be used with non-visible point light sources, such as near-infrared light, coupled with a detector. The thickness of the film and the size of the microparticle may be adjusted to compensate for the non-visible light source. Additionally, the present invention also provides a flexible support for an analyte-specific receptor layer either directly on the substrate or on gold or other suitable metal or metal alloy.

The present invention provides an analyte-specific receptor layer on gold or other material which is suitable for mass production. The biosensors used in the present invention can be produced as a single test for detecting an analyte or it can be formatted as a multiple test device. The biosensors of the present invention can be used to detect (1) antigens or antibodies associated with medical conditions, (2) contamination in garments, such as diapers, and (3) contamination by microorganisms.

In another embodiment of the present invention, nutrients for a specific class of microorganisms can be incorporated into the analyte-specific receptor layer. In this way, very low concentrations of microorganisms can be detected by first contacting the biosensor of the present invention with the nutrients incorporated therein and then incubating, if necessary, the biosensor under conditions appropriate for the growth of the bound microorganism. The microorganism is allowed to grow until there are enough organisms to form a diffraction pattern.

The present invention can also be used on contact lenses, eyeglasses, window panes, pharmaceutical vials, solvent containers, water bottles, adhesive bandages, and the like to detect contamination.

These and other features and advantages of the present invention will become apparent after a review of the following detailed description of the disclosed embodiments.

DETAILED DESCRIPTION

The present invention features improved biosensing devices, and methods for using such biosensing devices, for detecting and quantifying the presence or amount of an analyte of interest within a medium. The present invention is much more sensitive and can be used to detect smaller analytes which, until now, were not able to be detected without the use of expensive instruments. The analytes that can be detected by the present invention include, but are not limited to, hormones, proteins such as antibodies, steroids, drug metabolites, nucleic acids, microorganisms such as bacteria, yeasts, fungi and viruses. In contrast to prior devices, those of the present invention allow detection of extremely small quantities and sizes of analytes in a medium in a rapid assay lasting only a few minutes. In addition, no signaling or associated electronic components are required in the present invention.

The present invention comprises micro-contact printing of analyte-specific receptors onto polymer film, which may have a metal coating thereon. The invention allows for the development of single use, disposable biosensors based on light diffraction to indicate the presence of the analyte. Additionally, the present invention includes diffraction enhancing elements which increase the diffraction efficiency of the biosensor, thereby making it possible to detect any number of different analytes. Upon attachment of a target analyte to select areas of the polymer film which contain the receptor, either directly or in combination with a diffraction enhancing element, diffraction of transmitted and/or reflected light occurs via the physical dimensions and defined, precise placement of the analyte. For example, yeast, fungi or bacterium are large enough to act as diffraction elements for visible light when placed in organized patterns on a surface. However, smaller analytes, such as viruses, proteins, molecules, hormones, steroids, drug metabolites and nucleic acids, are only capable of acting as suitable diffraction elements when they are also bound to a diffraction enhancing element. In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern is discernible in less than one hour after contact of the analyte with the biosensing device of the present invention.

The diffraction grating which produces the diffraction of light upon interaction with the analyte and/or element should have a minimum periodicity of the wavelength of incident light. Very small analytes can be detected indirectly by using diffraction enhancing element particles that are specific for the small analyte. One embodiment in which the small analyte can be detected comprises coating the element particle, such as a latex bead, with a receptor material that specifically binds to the analyte of interest.

A variety of methods may be used to attach the receptor material onto the diffraction enhancing particle. These methods include, but are not limited to, simple physisorption to a hydrophobic particle (e.g., binding a protein onto polystyrene particles); binding using a protein A or protein G linker; binding using a streptavidin or avidin-biotin linker; or binding using covalent attachment. A preferred embodiment of the present invention is to use carbodiimide coupling of a proteinaceous receptor to carboxylated particles. Other methods of coupling well-known to those of ordinary skill in the art may be used as well.

Diffraction enhancing element particles that can be used in the present invention include, but are not limited to, glass, cellulose, synthetic polymers or plastics, latex, polystyrene, polycarbonate, bacterial or fungal cells and the like. The particles are preferably spherical in shape, but the structural and spatial configuration of the particle is not critical to the present invention. For instance, the particles could be slivers, ellipsoids, cubes, and the like. A desirable particle size ranges from a diameter of approximately 0.1 $\mu$m to 100.0 $\mu$m, desirably between approximately 0.3 $\mu$m to 1 $\mu$m. The composition of the element particle is not critical to the present invention. Preferably, the difference in refractive index between the medium and the enhancing element is between 0.1 and 1.0. More preferably, the difference in refractive index between the medium and the enhancing element is between 0.2 and 0.7

The analyte-specific receptor layer on the polymer film contains a receptive material, such as an antibody, that will specifically bind to an epitope on the analyte that is different from the epitope used in the binding to the particle. Thus, for detecting a small analyte, such as viral particles, the medium is first exposed to the diffraction enhancing element particles, such as latex particles, to which the viral particles bind. Then, the diffraction enhancing element particles are optionally washed and exposed to the polymer film with the analyte-specific receptor layers containing the virus specific antibodies. The antibodies then bind to the viral particles on the element particle thereby immobilizing the element particles in the same pattern as the receptors on the film. Because the bound element particles will cause diffraction of the visible light, a diffraction pattern is formed, indicating the presence of the viral particle in the liquid. Additionally, the polymer film may include a metal coating thereon. The analyte-specific receptor layer would then be located on the metalized surface of the film.

Alternatively, the analyte may be detected by first exposing the substrate to the medium containing the analyte and causing the analyte to bind to the analyte-specific receptor layer material. Next, a solution containing the diffraction enhancing element particles is contacted with the substrate having the analyte bound thereto. The particles then bind to the analyte. Because the bound element particles will cause diffraction of the visible light, a diffraction pattern is formed, indicating the presence of the analyte in the liquid.

Finally, in a preferred embodiment, the biosensor, the diffraction enhancing element particles and the medium containing the analyte may be admixed simultaneously. This will result in a combination of the binding procedures discussed above. Some of the analytes will first bind with a diffraction enhancing element particle prior to binding to the substrate. Other analytes will first bind with the substrate and then bind with an element particle. When a point-light source is shown through the sensor, a diffraction pattern is formed, indicating the presence of the analyte in the liquid.

The analytes that are contemplated as being detected using the present invention include, but are not limited to, bacteria; yeasts; fungi; viruses; rheumatoid factor; antibodies, including, but not limited to IgG, IgM, IgA and IgE antibodies; carcinoembryonic antigen; streptococcus Group A antigen; viral antigens; antigens associated with autoimmune disease; allergens; tumor antigens; streptococcus Group B antigen; HIV I or HIV II antigen; or host response (antibodies) to these and other viruses; antigens specific to RSV or host response (antibodies) to the virus; an antigen; enzyme; hormone; polysaccharide; protein; lipid; carbohydrate; drug or nucleic acid; Salmonella species; Candida species, including, but not limited to *Candida albicans* and *Candida tropicalis;* Salmonella species; *Neisseria meningitides* groups A, B, C, Y and W sub 135, *Streptococcus pneumoniae, E. coli* K1, *Haemophilus influenza* type B; an antigen derived from microorganisms; a hapten, a drug of abuse; a therapeutic drug; an environmental agent; and antigens specific to Hepatitis.

In another embodiment of the present invention, nutrients for a specific class of microorganisms can be incorporated into the analyte-specific receptor layer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern. Of course, in some cases, the microorganism is present or can multiply enough to form a diffraction pattern without the presence of a nutrient on the patterned monolayer.

A part of the present invention is the analyte-specific receptor material that can be microprinted on the polymer film and will specifically bind to the analyte of interest. Thus, the receptor material is defined as one part of a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species. Additionally, when a metalized polymer film is used, the analyte-specific receptor material can be microprinted on the metalized surface of the film.

The receptor material that is bound to the attachment layer is characterized by an ability to specifically bind the analyte or analytes of interest. The variety of materials that can be used as receptor material are limited only by the types of material which will combine selectively (with respect to any chosen sample) with the analyte. Subclasses of materials which can be included in the overall class of receptor materials includes toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, and any other member of a specific binding pair. This list only incorporates some of the many different materials that can be coated onto the attachment layer to produce a thin film assay system. Whatever the selected analyte of interest is, the receptor material is designed to bind with the analyte of interest. In the preferred embodiments, the biosensing device is configured and arranged to provide a pattern detectable by eye in response to transmission of a point light source when the analyte of interest is sandwiched between the receptor material and a diffraction enhancing element.

In many instances, a "blocker" may be necessary to prevent non-specific binding. The term "blocker" as used herein means a reagent that adheres to the sensor surface so that it "blocks" or prevents non-analyte materials from binding to the surface (either in the patterned or un-patterned areas). The blocking step may be done as a post-treatment to a surface which has already been contact printed ("post-block"), and is the standard technique for filling in non-contact printed regions with another thiol. However, the inventors have discovered that a "pre-block" technique is preferred over the post-block technique. In the pre-block technique, the surface of the substrate is pre-treated with a non-thiol containing blocker and then contact printed. Not wishing to be bound to any theory, it is theorized that the contact printed material (usually sulfur containing) displaces the physisorbed blocker, thereby permitting the analyte-specific receptor material to be bound directly to the surface of the substrate. A subsequent post-block may also be performed, if desired. Blockers can include, but are not limited to, β-casein, albumins such as bovine serum albumin, pluronic or other surfactants, polyethylene glycol, polyvinyl alcohol, or sulfur derivatives of the above compounds, and any other blocking material known to those of ordinary skill in the art.

The matrix containing the analyte of interest may be an interstitial fluid, a solid, a gas, or a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, a throat swab or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material. For example, receptor material for bacteria may specifically bind a surface membrane component, protein or lipid, a polysaccharide, a nucleic acid, or an enzyme. The analyte which is indicative of the bacteria may be a saccharide or polysaccharide, an enzyme, a nucleic acid, a membrane component, a ganglioside or an antibody produced by the host in response to the bacteria. The presence of the analyte may indicate an infectious disease (bacterial or viral), cancer, an allergy, or other medical disorder or condition. The presence of the analyte may be an indication of water or food contamination or other harmful materials. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For immunoassays, an antibody may serve as the receptor material and/or it may be the analyte of interest. The receptor material, for example an antibody or an antigen, must form a stable, reactive layer on the attachment layer of the test device. If an antibody is the receptor material, the antibody must be specific to the antigen of interest; and the antibody (receptor material) must bind the antigen (analyte) with sufficient avidity that the antigen is retained at the test surface. In some cases, the analyte may not simply bind the receptor material, but may cause a detectable modification of the receptor material to occur. This interaction could cause an increase in mass at the test surface or a decrease in the amount of receptor material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptor material occurs is not important to this invention, but may impact the reaction conditions used in the final assay protocol.

In general, the receptor material may be passively applied to the substrate layer. If required, the free functional groups introduced onto the test surface by the attachment layer may be used for covalent attachment of receptor material to the test surface.

A wide range of techniques can be used to apply the receptor material to the substrate layer. Test surfaces may be coated with receptor material by application of solution in discrete arrays or patterns; spraying, ink jet, contact printing or other imprinting methods; or printing a blocker material in a pattern followed by total immersion or spin coating with the receptor material. The technique selected should minimize the amount of receptor material required for coating a large number of test surfaces and maintain the stability/functionality of receptor material during application. The technique must also apply or adhere the receptor material to the attachment layer in a very uniform and controlled fashion.

The biosensing device of the present invention utilizes methods of contact printing of patterned, analyte-specific receptor layers on polymer or metalized polymer films, desirably transparent or semi-transparent, the compositions produced thereby, and the use of these compositions. Patterned analyte-specific receptor layers allow for the controlled attachment (or binding) placement of the analyte receptor. The term "patterned analyte-specific receptor layers thereon" as used herein means the analyte-specific receptor layers in any pattern on the polymer or metalized polymer films, including a solid pattern.

When the film with the patterned analyte-specific receptor layers thereon is exposed to an analyte that is capable of reacting with the analyte-specific receptor layer, the film will produce optical diffraction patterns which differ depending on the reaction of the patterned analyte-specific receptor layer with the analyte of interest. The medium would contain the diffraction enhancing element particles. The medium may be a high surface tension fluid such as water. The light can be in the visible spectrum, and be either reflected from the film, or transmitted through it, and the analyte can be any compound reacting with the analyte-specific receptor layer.

In preferred embodiments, the method involves contacting the sensing device with a test sample containing the diffraction enhancing element particles and potentially containing the analyte. If the analyte is present in the sample, then when light is transmitted through a metalized polymer film with the analyte-specific receptor layer, a visible diffraction image is formed.

The medium in which the analyte may reside can be solid, gel-like, liquid or gas. For purposes of detecting an analyte in a body fluid, the fluid is selected from, but not limited to, urine, serum, plasma, spinal fluid, sputum, whole blood, saliva, uro-genital secretions, fecal extracts, pericardial, gastric, peritoneal, pleural washes, vaginal secretions, or a throat swab. The most common gas that is contemplated as being used with the biosensing device of the present invention is air In one embodiment, the present invention is contemplated in a dipstick form in which a micro-contact printed metalized film is mounted at the end of the dipstick. In use, the dipstick is dipped into the liquid in which the suspected analyte may be present. The liquid would also contain the diffraction enhancing element particles. The dipstick is allowed to remain for several minutes. The dipstick is then removed and then, either a light is projected through the metalized film or the film is observed with a light behind the film. If a diffraction image is observed, then the analyte is present in the liquid.

Figure 1:
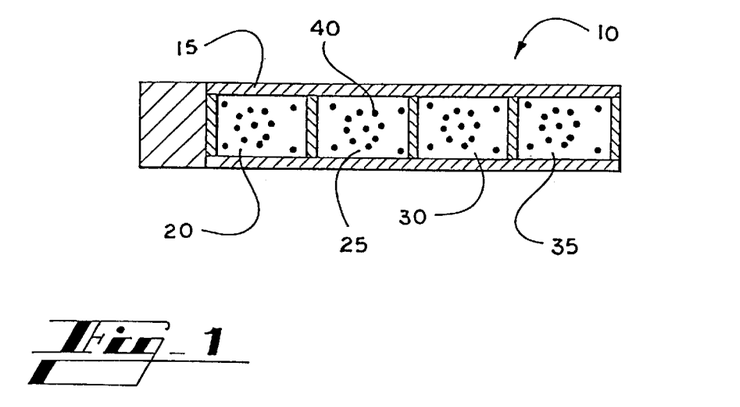
FIG. 1 shows a biosensor capable of simultaneously measuring several different analytes in a medium.

In another embodiment of the present invention, a multiple analyte test is constructed on the same support. As shown in FIG. 1, a strip 10 is provided with several micro-contact printed films 20, 25, 30 and 35, each film having a pattern 40 printed thereon. Each of the micro-contact printed films 15, 20, 25, and 30 have a different receptor material that is specific for different analytes. It can be seen that the present invention can be formatted in any array with a variety of micro-contact printed films thereby allowing the user of the biosensor device of the present invention to detect the presence of multiple analytes in a medium using a single test.

There are many possible supports for the analyte-specific receptor layers. Simple physisorption can occur on many materials, such as polystyrene glass, nylon, or others well known to those of ordinary skill in the art. Preferred embodiments of immobilizing the analyte-specific receptor layers have involved covalent attachment, such as that possible between thiol or disulfide-containing compounds and gold. Typically, a gold coating, 5 to 2000 nm thick, is supported on a $Si/SiO_2$ wafer, glass, or a polymer film. Optionally, titanium can be used to serve as an adhesion promoter between gold and the support. The analyte-specific receptor attaches to the gold surface during contact printing or immersion from a solution. Preferably, the support comprises a gold coating on a MYLAR® film.

Figure 2:
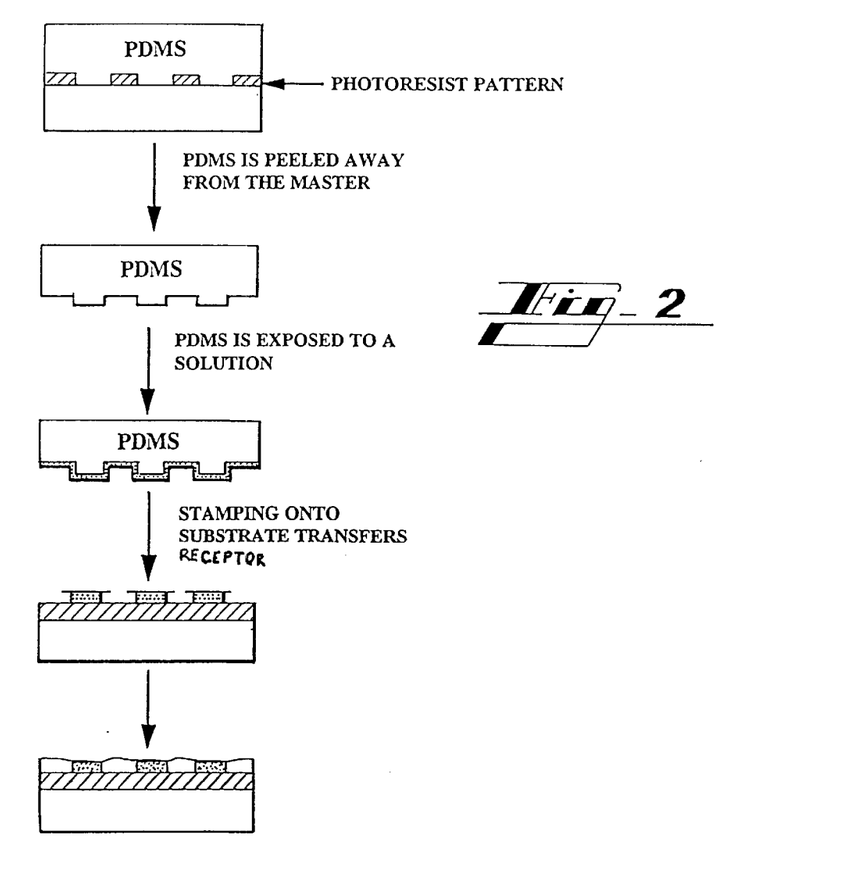
FIG. 2 is a schematic of contact printing of analyte-specific receptor layers.
Figure 3:
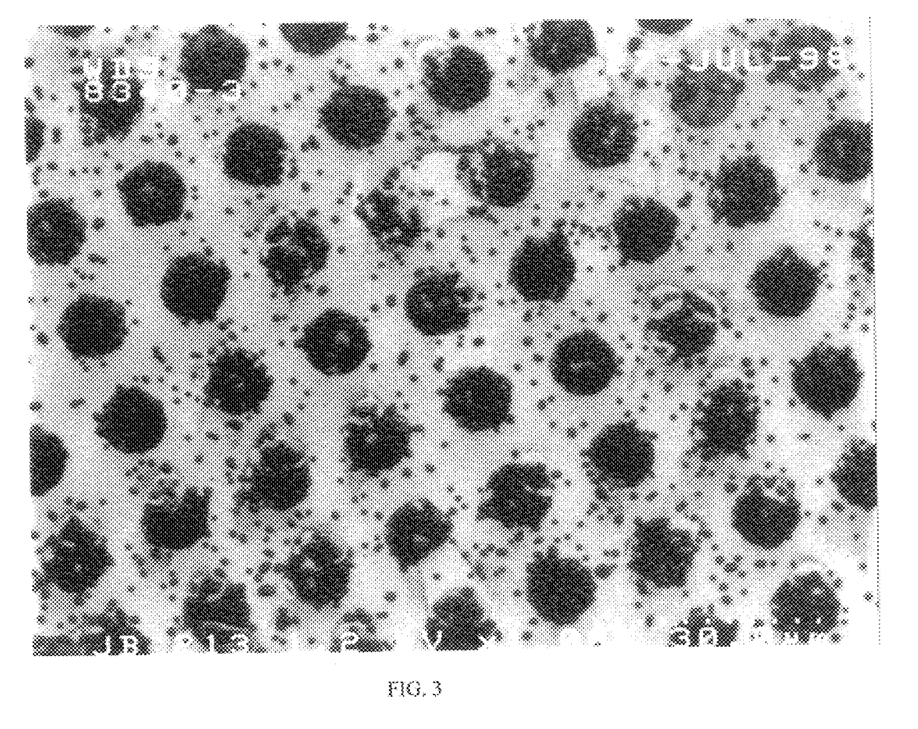
FIG. 3 is an atomic force microscopy image of evaporated gold on MYLAR®, purchased from Courtaulds Performance Films (Canoga Park, Calif.). The average roughness of the gold layer is 3–4 nanometers, with maximum roughness of 9 nanometers.

FIG. 2 outlines the procedure used for microcontact printing. An elastomeric stamp is used to transfer analyte-specific receptor "ink" to a gold surface by contact; if the stamp is patterned, a patterned analyte-specific receptor layer forms. The stamp is fabricated by casting polydimethylsiloxane (PDMS) on a master having the inverse of the desired pattern. Masters are prepared using standard photolithographic techniques, or constructed from existing materials having microscale surface features.

In a preferred embodiment of a typical experimental procedure, a photolithographically produced master is placed in a glass or plastic Petri dish, and a 10:1 ratio (w:w) mixture of SYLGARD® silicone elastomer 184 and SYLGARD® silicone elastomer 184 curing agent (Dow Corning Corporation) is poured over it. The elastomer is allowed to sit for approximately 30 minutes at room temperature and reduced pressure to degas, then cured for at least 4 hours at 60° C., and gently peeled from the master. "Inking" of the elastomeric stamp is accomplished by exposing the stamp to a 0.1 to 10 $\mu$M aqueous solution of disulfide-derivatized antibody typically by placing the stamp face down in the solution for 10 seconds to 10 minutes. The stamp is allowed to dry, either under ambient conditions, or typically by exposure to a stream of air or nitrogen gas. Following inking, the stamp is applied to a gold surface. Light pressure is used to ensure complete contact between the stamp and the surface. After 1 second to 5 minutes, the stamp is then gently peeled from the surface. Following removal of the stamp, the surface is rinsed and dried. Alternatively, further derivatization of unstamped areas can be accomplished, either by using a second stamp or by exposing the entire surface with a different reagent. Subsequently, exposure to a protein-blocking agent, such as BSA or $\beta$-casein, or any other agent well known in the art, can also be done.

The elastomeric character of the stamp is important to the success of the process. Polydimethylsiloxane (PDMS), when cured, is sufficiently elastomeric to allow good conformal contact of the stamp and the surface, even for surfaces with significant relief; this contact is essential for efficient contact transfer of the receptor to a gold film. The elastomeric properties of PDMS are also important when the stamp is removed from the master: if the stamp were rigid (as is the master) it would be difficult to separate the stamp and master after curing without damaging one of the two substrates. PDMS is also sufficiently rigid to retain its shape, even for features with sub-micron dimension. The stamp is durable in that the same stamp can be used over 200 times over a period of a year without significant degradation in performance. Using a printing roll for the stamp could allow for a continuous printing operation. Alternatively, ink-jet printing of the desired pattern could also be done if capable of producing the feature sizes needed for diffraction, for example $\leq 100$ μm.

A more detailed description of the methods and compositions of the present invention follows. All publications cited herein are incorporated by reference in their entirety.

Any plastic film is suitable for the present invention. Preferably, the plastic film is also capable of having a metal coating deposited thereon. These include, but are not limited to polymers such as: polyethylene-terephthalate (e.g., MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable plastics and suppliers may be found, for example, in reference works such as the *Modern Plastics Encyclopedia* (McGraw-Hill Publishing Co., New York 1923–1996).

In one embodiment of the invention, the polymer film has a metal coating thereon and has an optical transparency of between approximately 5% and 95%. A more desired optical transparency for the plastic film used in the present invention is between approximately 20% and 80%. In a desired embodiment of the present invention, the polymer film has at least an approximately 80% optical transparency, and the thickness of the metal coating is such as to maintain an optical transparency greater than about 60%, so that diffraction images can be produced by transmitted light. This corresponds to a metal coating thickness of about 10 nm. However, in other embodiments of the invention, the gold thickness may be between approximately 1 nm and 1000 nm; for example, thicker gold coatings (>20 nm) would still be suitable for producing diffraction images by reflected light.

The preferred metal for deposition on the film is gold. However, silver, aluminum, chromium, copper, iron, zirconium, platinum and nickel, as well as oxides of these metals, may be used.

In principle, any surface with corrugations of appropriate size could be used as masters. The process of microcontact printing starts with an appropriate relief structure, from which an elastomeric stamp is cast. This 'master' template may be generated photolithographically, or by other procedures, such as commercially available diffraction gratings. In one embodiment, the stamp may be made from polydimethylsiloxane.

The stamp may be applied in air, or under a fluid capable of preventing excess diffusion of the receptor material. For large-scale or continuous printing processes, it is most desirable to print in air.

In one embodiment of the present invention, the pattern is formed on the metalized plastic polymer with the analyte-specific receptor layer. After the stamping process, the metalized areas on the plastic may optionally be blocked, for example, with a protein-repelling agent such as β-casein.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

Antibody-conjugated polystyrene particles were produced by carbodiimide coupling with ethyldimethylaminodicarbodiimide (EDAC, bottle #3 of Polysciences kit, Catalog #19539). For this example, 0.125 mL of a 10% suspension of 0.5 micron diameter blue carboxylated particles (Bangs Laboratories, Fishers, Ind., Cat #D0005070CB) were activated with an aqueous solution of the EDAC for 1–4 hours, rinsed, then exposed to 300 micrograms of a monoclonal antibody to luteinizing hormone, alpha subunit, (Fitzgerald Industries, Concord, Mass., Cat#10-L10, Clone #M94136). The particles were again rinsed, blocked with bovine serum albumin, and stored at 2.5% concentration in phosphate buffered saline.

Next, a gold/MYLAR® film was pre-treated (or blocked) with a 5 mg/mL beta casein solution for 10 minutes, then thoroughly rinsed and dried under an air stream. A PDMS stamp of 10-micron circles was coated with thiolated antibody by placing the stamp face down in a 0.5 mg/mL thiolated antibody solution and soaking for 10 minutes. A strong air stream was used to thoroughly dry the surface of the stamp. The coated stamp was placed in contact with the gold/MYLAR® film for 5 minutes, then removed. The resulting printed gold/MYLAR® film was rinsed in distilled water, and dried.

A 10 mM stock solution of the Sulfo-LC-SPDP is prepared by dissolving 1.3 mg Sulfo-LC-SPDP into 2.07 ml de-ionized water. The conjugation reaction is carried out in phosphate buffered saline (PBS) containing 20 mM sodium phosphate buffer, 150 mM NaCl, 1 mM EDTA and 0.02% sodium azide at pH 7.5. One milligram of lyophilized antibody is dissolved in 450 ml PBS, and 50 ml of Sulfo-LC-SPDP stock solution is added to the antibody solution. The mixture is allowed to react at room temperature for 60 minutes. The sample is applied to a 5 ml desalting polyacrylamide column previously equilibrated with 5 bed volumes (25 ml) of PBS. Fractions are eluted using PBS as the elution buffer, and the protein in the fractions is monitored using a COOMASSIE® Protein Assay (Pierce Chemical Co). Typically, 50 ul of the COOMASSIE® reagent is mixed with 50 ul of each fraction in a micro-titer plate. The COOMASSIE® Blue substrate reacts with the protein, producing a blue color, the intensity of which is dependent upon the amount of protein present in the fraction. The fractions which produce the most intense blue color are those containing the majority of the protein eluted. These fractions are pooled together to produce the disulfide form of the final derivatized product. This is typically the form used for contact printing.

Optionally, the disulfide-pyridyl group present on the disulfide form of the thiolated binder can be reduced to a thiol group in a reduction reaction. Instead of desalting on a column equilibrated with PBS, the derivatized protein is desalted on a column equilibrated with an acetate buffer (100 mM sodium acetate buffer, 100 mM NaCl, pH 4.5). The acidic pH of this acetate buffer acts to protect any disulfide bonds present on the native protein from undesired reduction. In the reduction reaction, 12 mg of dithiothreitol (DTT) is dissolved in 500 ml acetate buffer and added to 1 ml of the SPDP derivatized protein. The reaction mixture is incubated for 30 minutes at room temperature, and desalted on a 5 ml desalting column equilibrated with 5 bed volumes (25 ml) of acetate buffer. The protein content of the fractions eluted is again monitored by the COOMASSIE® Protein Assay as described above, and the fractions containing the greatest amount of protein are pooled.

Both the disulfide and reduced forms of the thiolated binders are stored in aqueous solution at 4° C. until used for contact printing.

The sensors were then used to detect an analyte. The analyte solution was then mixed with microparticles (typically 50–70 microliters of analyte solution in 1% bovine serum albumin with 10–25 microliters of 1.5–2.5% particle suspension; preferably, there is a 50:25 ratio of analyte solution to particle suspension), and placed on top of a 1 cm square sensor sample. After 5 minutes, a nitrocellulose disk (5 or 8 micron pore size, Sigma #N3771 or N4146) with a small hole (e.g. $3/16''$) punched out of the center was placed on top of the sensor. The disk was used to wick away excess fluid and unbound microparticles. At this time, a point light source was transmitted through the sensor sample (using the small hole in the nitrocellulose). A diffraction image would be seen on the other side of the light beam in the presence of the target analyte.

Figure 4:
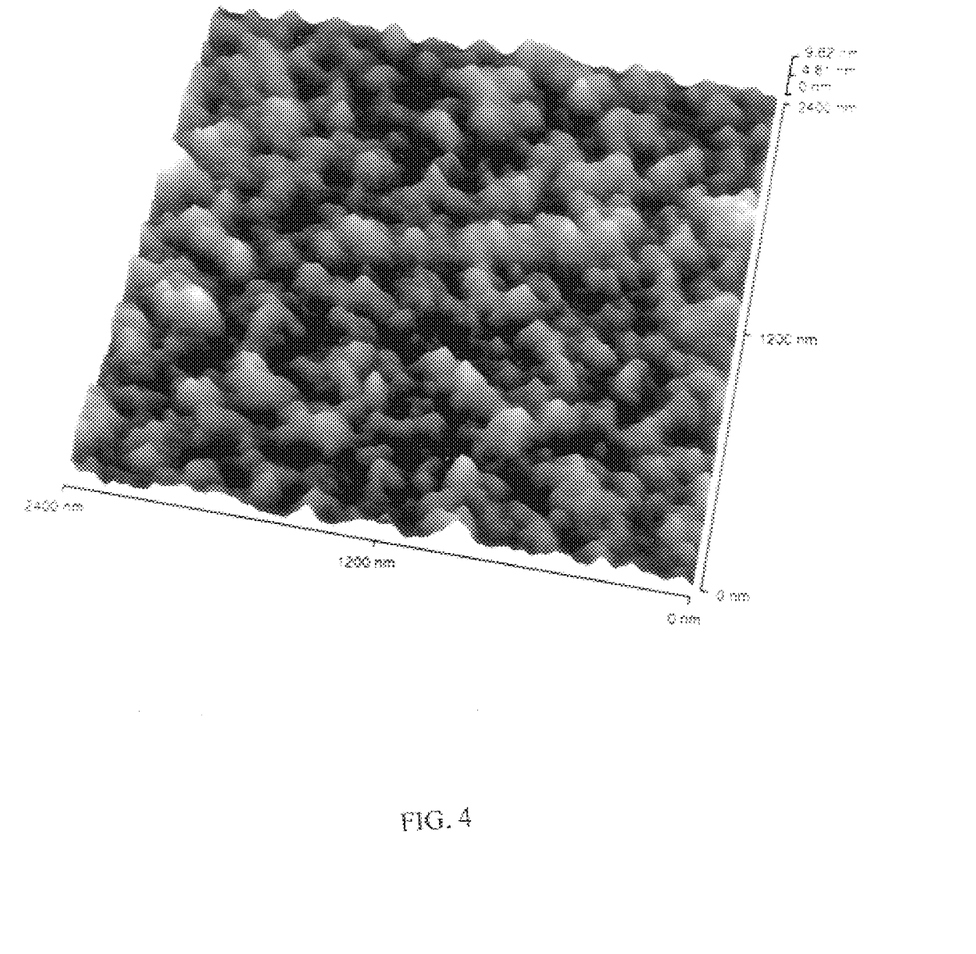
FIG. 4 is an SEM photomicrograph showing patterned attachment of diffraction enhancing elements in the presence of an analyte.

As seen in FIG. 4, SEM photomicrographs showed the patterned placement of the microparticles.

Example 2

A PDMS stamp of an x,y array of 10-micron circles was "inked" with thiolated 30-mer oligonucleotide which is complementary to the target DNA strand ("30-mer"; base sequence of thiol spacer-5'-CAATCCACGTCACGGACAGGGTGAGGAAGA-3' made by Genosys, Inc., The Woodlands, Tex.) by placing the stamp face down with weight in oven-dried (50° C., vacuum) mixture of the 30-mer and ethyl acetate on glass. After 10 minutes, the inked stamp was removed. At the same time, a gold/MYLAR® film was pre-heated on a 60° C. hot plate for 5 minutes. Printing was done by placing the inked PDMS stamp on top of the gold-coated side of MYLAR® at 60° C.; weight and heat were maintained during the 5 minute contact time. At this point, the stamp was removed and the printed gold/MYLAR® film was washed with distilled water, and air-dried. The gold/MYLAR® film sample was then blocked with a 2.5 mg/mL beta casein solution (in phosphate buffered saline, pH 7.2) for 10 minutes, and rinsed with distilled water and air-dried.

These sensors were used to test for target DNA. Hybridization of the target DNA to the capture DNA patterned on the sensor surface took place as follows: A pre-heated analyte solution (60° C. water bath, 2 minutes) containing a DNA strand of interest (a biotinylated 70-mer from Genosys with base sequence of biotin-5'-GGTAGACCGGAGAGCTGTGTCACCAT-GTGGGTCCCGG TTGTCTTCCTCACCCTGTCCGTGACGTGGATTG-3') was added to a pre-heated sensor (60° C. hot plate, 5 minutes) and then 75 microliters was added to an approximately 1 cm square sensor for an additional 10 minutes heating. After this time, the sensor sample was rinsed with water, and air-dried for subsequent testing with microparticles. One variation to this method is that the analyte solution, e.g., during a PCR amplification, and the microparticles are exposed to the sensor at the same time.

Next, Streptavidin-coated, 1 micron diameter particles from Bangs Laboratories (Catalog #CP01N) were added in 20–30 microliter amounts, concentration of $2.4 \times 10^{11}$ particles per mL, to the sensor. The sensor and particles were heated on a 60° C. hot plate for 10 minutes (covered, while ensuring that complete evaporation did not take place), and then rinsed gently with distilled water. After this, a point light source was transmitted through the sensor sample. A diffraction image would be seen on the other side of the light beam in the presence of the DNA analyte.

SEM photomicrographs show the patterned placement of the microparticles.

Example 3

Antibody-conjugated polystyrene particles were produced by carbodiimide coupling with ethyldimethylaminodicarbodiimide ("EDAC", bottle #3 of Polysciences kit, Catalog #19539). For example, 0.125 mL of a 10% suspension of 0.3 micron diameter blue carboxylated particles (Bangs Laboratories, Cat #DC02/1836) were activated with an aqueous solution of the EDAC for 1–4 hours, rinsed, then exposed to 300 micrograms of a polyclonal antibody to IgE (Fitzgerald Industries, Cat#20-IR77). The particles were again rinsed, blocked with bovine serum albumin, and stored at 1.7% concentration in phosphate buffered saline.

Next, a gold/MYLAR® film was pre-treated (or blocked) with a 5 mg/mL beta casein solution for 10 minutes, then thoroughly rinsed and dried under an air stream. A PDMS stamp of an x,y array of 10-micron diameter circles was coated with thiolated antibody (antibody was initially Fitzgerald Catalog #10-I10 then derivatized or "thiolated" using Sulfo-LC-SPDP by Pierce) by placing the stamp face down in a 0.5 mg/mL thiolated antibody solution and soaking for 10 minutes. A strong air stream was used to thoroughly dry the surface of the stamp. The coated stamp was placed in contact with the gold/MYLAR® film for 5 minutes, then removed. The resulting printed gold/MYLAR® film was rinsed in distilled water, and dried.

The analyte solution was then mixed with microparticles (typically 50–70 microliters of analyte solution in 1% bovine serum albumin with 10–25 microliters of 1.5–2.5% particle suspension; preferably, there is a 50:25 ratio of analyte solution to particle suspension), and placed on top of a 1 cm square sensor sample. After 5–10 minutes, a nitrocellulose disk (5 or 8 micron pore size, Sigma #N3771 or N4146) with a small (e.g., $3/16''$ diameter) hole punched out of the center is placed on top of the sensor. The disk was used to wick away excess fluid and unbound microparticles. At this time, a point light source was transmitted through the sensor sample by taking advantage of the small hole in the nitrocellulose. A high order diffraction image was seen on the other side of the light beam, signifying the presence of the analyte.

Example 4

A gold/MYLAR® film was pre-treated (or blocked) with a 5 mg/mL beta casein solution in phosphate buffered saline (pH~7.2) for 10 minutes, then thoroughly rinsed and dried under an air stream. A PDMS stamp of 10-micron circles was coated with thiolated antibody (e.g., rabbit anti-*Candida albicans,* Cat #20-CR04 from Fitzgerald Industries, Inc.) by placing the stamp face down in a 0.5 mg/mL thiolated antibody solution and soaking for 10 minutes. A strong air stream was used to thoroughly dry the surface of the stamp. The coated stamp was placed in contact with the gold/MYLAR® film for 2 minutes, then removed. The resulting printed gold/MYLAR® film was rinsed in distilled water, and dried.

The sensor sample was exposed to a 10% dilution in phospate buffered saline, pH 7.2 of 40 nm gold particles coated with goat anti-rabbit IgG (gold conjugate was from Polysciences, Catalog #22705). After one hour, the samples were thoroughly rinsed with distilled water and dried under a nitrogen or air stream. At this point, the samples do not diffract a HeNe laser beam.

The samples were then exposed to silver enhancing reagents from BBI (either BBI International's kit #SEKL 15 (Batch #2575) or large kit #SEKB250 (Batch #2484) were used). A 1:1 v/v ratio of the enhancer and initiator reagents in the kit were pre-mixed and then immediately placed on top of the gold-particle coated samples. After 10–20 minutes exposure (preferably, 10 minutes), the samples were rinsed with water, dried, and examined. At this point, the samples diffracted light (either a laser beam or a point white light source) most likely due to the larger size of the silver nucleated around the gold nanoparticles.

Example 5

Samples prepared as per Examples 1 or 4 could also be developed into a diffraction image by exposing it to an enzyme-conjugate secondary antibody in the presence of the analyte, such that if the analyte is present the secondary antibody would bind and cause subsequent precipitate development with a precipitating substrate specific to the enzyme.

A gold/MYLAR® film was pre-treated (or blocked) with a 5 mg/mL beta casein solution in phosphate buffered saline (pH~7.2) for 10 minutes, then thoroughly rinsed and dried under an air stream. A PDMS stamp of 10-micron circles was coated with thiolated antibody (e.g., mouse anti-luteinizing hormone beta, Cat #10-L15 from Fitzgerald Industries, Inc.) by placing the stamp face down in a ~0.3 mg/mL thiolated antibody solution and soaking for 10 minutes. A strong air stream was used to thoroughly dry the surface of the stamp. The coated stamp was placed in contact with the gold/MYLAR film for 5 minutes, then removed. The resulting printed gold/MYLAR® film was rinsed in distilled water, and dried.

The sensor sample was exposed to an analyte solution of luteinizing hormone (Cat #30-AL15 from Fitzgerald Industries, Inc.) in 1% bovine serum albumin, phosphate buffered saline. Concentration of antigen was varied from 0.1 to 1000 ng/mL. After one hour at room temperature, the sample was rinsed with 0.02% TWEEN 20 solution, then distilled water. A subsequent exposure to a secondary antibody (Fitzgerald Catalog #61-L05 diluted 1:100 in distilled water) for one hour was done, followed by rinsing as above. A TMB membrane enhancer solution (e.g., a 10:1 v/v mixture of Kirkegaard and Perry Laboratories' reagents Cat #50-76-18 and Cat#50-77-01) was placed on the sample for 10 minutes to cause development of a blue precipitate in the circles or features. This precipitate caused a diffraction image to form upon irradiation with a point light source.

We claim:

1. A system for detecting an analyte in a medium comprising:
   a diffraction enhancing element having a receptor material thereon that is specific for the analyte; and
   a sensing device comprising:
      a polymer film; and
      an analyte-specific receptor layer printed in a pattern onto the polymer film wherein the analyte-specific receptor layer has a receptor material thereon that is specific for the analyte;
   wherein the analyte-specific receptor layer is printed in a pattern such that when the sensing device binds an analyte, the sensing device diffracts transmitted light to form a diffraction pattern;
   wherein the diffraction pattern is visible to an unaided eye.

2. The system of claim 1, further comprising a metal coating on the polymer film and wherein the analyte-specific receptor layer is printed onto the metal coating.

3. The system of claim 2, wherein the metal coating is selected from gold, silver, chromium, nickel, platinum, aluminum, iron, copper, gold oxide, chromium oxide or zirconium.

4. The system of claim 3, wherein the metal coating is gold.

5. The system of claim 4, wherein the gold coating is between approximately 1 nanometer and 1000 nanometers in thickness.

6. The system of claim 1, wherein the polymer film is selected from polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, polyethylene, polyethylene-vinyl acetate copolymers, ionomers (ethylene polymers) polyethylene-nylon copolymers, polypropylene, methyl pentene polymers, polyvinyl fluoride, or aromatic polysulfones.

7. All The system of claim 6, wherein the polymer film is polyethylene-terephthalate.

8. The system of claim 1, wherein the polymer film is optically transparent.

9. The system of claim 8, wherein the polymer film has an optical transparency between 5% and 95%.

10. The system of claim 8, wherein the polymer film has an optical transparency between approximately 20% and 80%.

11. The system of claim 1, wherein there are two or more analyte-specific receptor layers with each layer having different chemical properties.

12. The system of claim 1, wherein the analyte is selected from bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies viruses, antigens specific to RSV, an antibody, antigen, enzyme, hormone, polysaccharide, protein, lipid, carbohydrate, drug or nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agent, or antigens specific to Hepatitis.

13. The system of claim 12, wherein the analyte is bacteria, yeast, fungus or virus.

14. The system of claim 1, wherein the receptor material is selected from antigens, antibodies, oligonucleotides, chelators, enzymes, bacteria, yeasts, fungi, viruses, bacterial pili, bacterial flagellar materials, nucleic acids, polysaccharides, lipids, proteins, carbohydrates, metals, hormones or receptors for said materials.

15. The system of claim 1, wherein the diffraction enhancing element is selected from glass, cellulose, synthetic polymers or plastics, latex, polystyrene, polycarbonate, bacterial or fungal cells.

16. The system of claim 1, wherein the diffraction enhancing element is polystyrene latex microspheres.

17. The system of claim 1, further comprising a blocking material applied to the non-printed areas of the polymer film.

18. The system of claim 17, wherein the blocking material is selected from β-casein, an albumin, a surfactant, polyethylene glycol, polyvinyl alcohol, or sulfur derivatives thereof.

19. The system of claim 1, wherein the sensing device further comprises a layer of blocking material on the polymer film through which the analyte-specific receptor material is printed.

20. The system of claim 19, wherein the blocking material is selected from β-casein, an albumin, a surfactant, polyethylene glycol, polyvinyl alcohol, or sulfur derivatives thereof.

21. A system for detecting an analyte in a medium comprising:
a diffraction enhancing element having a receptor material thereon that is specific for the analyte; and
a sensing device comprising:
a polymer film coated with metal; and
an analyte-specific receptor layer printed in a pattern onto the polymer film wherein the analyte-specific receptor layer has a receptor material thereon that is specific for the analyte;
wherein the analyte-specific receptor layer is printed in a pattern such that when the sensing device binds an analyte, the sensing device diffracts reflected light to form a diffraction pattern;
wherein the diffraction pattern is visible to an unaided eye.

22. The system of claim 21, wherein the metal coating is selected from gold, silver, chromium, nickel, platinum, aluminum, iron, copper, gold oxide, chromium oxide or zirconium.

23. The system of claim 22, wherein the metal coating is gold.

24. The system of claim 23, wherein the gold coating is between approximately 1 nanometer and 1000 nanometers in thickness.

25. The system of claim 21, wherein the polymer film is selected from polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, polyethylene, polyethylene-vinyl acetate copolymers, ionomers (ethylene polymers) polyethylene-nylon copolymers, polypropylene, methyl pentene polymers, polyvinyl fluoride, or aromatic polysulfones.

26. The system of claim 25, wherein the polymer film is polyethylene-terephthalate.

27. The system of claim 21, wherein there are two or more analyte-specific receptor layers with each layer having different chemical properties.

28. The system of claim 21, wherein the analyte is selected from bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies viruses, antigens specific to RSV, an antibody, antigen, enzyme, hormone, polysaccharide, protein, lipid, carbohydrate, drug or nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agent, or antigens specific to Hepatitis.

29. The system of claim 28, wherein the analyte is bacteria, yeast, fungus or virus.

30. The system of claim 21, wherein the receptor material is selected from antigens, antibodies, oligonucleotides, chelators, enzymes, bacteria, yeasts, fungi, viruses, bacterial pili, bacterial flagellar materials, nucleic acids, polysaccharides, lipids, proteins, carbohydrates, metals, hormones or receptors for said materials.

31. The system of claim 21, wherein the diffraction enhancing element is selected from glass, cellulose, synthetic polymers or plastics, latex, polystyrene, polycarbonate, bacterial or fungal cells.

32. The system of claim 21, wherein the diffraction enhancing element is polystyrene latex microspheres.

33. The system of claim 21, further comprising a blocking material applied to the non-printed areas of the polymer film.

34. The system of claim 33, wherein the blocking material is selected from β-casein, an albumin, a surfactant, polyethylene glycol, polyvinyl alcohol, or sulfur derivatives thereof.

35. The system of claim 21, wherein the sensing device further comprises a layer of blocking material on the metal-coated polymer film through which the analyte-specific receptor material is printed.

36. The system of claim 35, wherein the blocking material is selected from β-casein, an albumin, a surfactant, polyethylene glycol, polyvinyl alcohol, or sulfur derivatives thereof.

37. A system for detecting an analyte in a medium comprising:
a diffraction enhancing element having a receptor material thereon that is specific for the analyte; and
a sensing device comprising:
a polymer film coated with metal; and
an analyte-specific receptor layer printed in a pattern onto the metal-coated polymer film wherein the analyte-specific receptor layer has a receptor material thereon that is specific for the analyte;
wherein the analyte-specific receptor layer is printed in a pattern such that when the sensing device binds an analyte, the sensing device diffracts transmitted light to form a diffraction pattern;
wherein the diffraction pattern is visible to an unaided eye.

* * * * *